(12) United States Patent
Busman

(10) Patent No.: US 11,844,364 B2
(45) Date of Patent: Dec. 19, 2023

(54) THERAPEUTIC COMPOSITION INCLUDING CARBONATED SOLUTION

(71) Applicant: VISION PHARMA, LLC, Estero, FL (US)

(72) Inventor: Sander S. Busman, Naples, FL (US)

(73) Assignee: VISION PHARMA, LLC, Estero, FL (US)

( * ) Notice: Subject to any disclaimer, the term of this patent is extended or adjusted under 35 U.S.C. 154(b) by 128 days.

(21) Appl. No.: 16/821,421

(22) Filed: Mar. 17, 2020

(65) Prior Publication Data

US 2020/0214322 A1 Jul. 9, 2020

Related U.S. Application Data

(62) Division of application No. 14/161,489, filed on Jan. 22, 2014, now Pat. No. 10,595,550.

(51) Int. Cl.

| | |
|---|---|
| A61K 36/00 | (2006.01) |
| A61K 45/06 | (2006.01) |
| A23L 2/54 | (2006.01) |
| A61K 31/167 | (2006.01) |
| A61K 31/197 | (2006.01) |
| A61K 31/439 | (2006.01) |
| A61K 31/4402 | (2006.01) |
| A61K 31/192 | (2006.01) |
| A61K 31/135 | (2006.01) |
| A61K 31/137 | (2006.01) |
| A61K 31/4545 | (2006.01) |
| A61K 31/5415 | (2006.01) |
| A61K 36/74 | (2006.01) |
| A61K 31/4965 | (2006.01) |
| A61K 31/522 | (2006.01) |
| A23L 33/10 | (2016.01) |

(52) U.S. Cl.
CPC .............. *A23L 2/54* (2013.01); *A23L 33/10* (2016.08); *A61K 31/135* (2013.01); *A61K 31/137* (2013.01); *A61K 31/167* (2013.01); *A61K 31/192* (2013.01); *A61K 31/197* (2013.01); *A61K 31/439* (2013.01); *A61K 31/4402* (2013.01); *A61K 31/4545* (2013.01); *A61K 31/4965* (2013.01); *A61K 31/522* (2013.01); *A61K 31/5415* (2013.01); *A61K 36/74* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,729,997 | A * | 3/1988 | Wenig | A61K 9/0043 |
| | | | | 514/226.2 |
| 2008/0220092 | A1 | 9/2008 | Dipierro | |
| 2009/0264475 | A1 * | 10/2009 | Schwartz | A23L 33/30 |
| | | | | 514/343 |
| 2012/0128857 | A1 * | 5/2012 | Kitsutaka | A23C 11/103 |
| | | | | 426/598 |
| 2012/0245231 | A1 | 9/2012 | Kaplan | |
| 2015/0327585 | A1 * | 11/2015 | Domoto | A61K 47/36 |
| | | | | 426/590 |
| 2020/0230120 | A1 * | 7/2020 | Worthington | A61K 31/407 |

FOREIGN PATENT DOCUMENTS

| | | |
|---|---|---|
| EP | 222967 A | 5/1987 |
| FR | 2934780 A1 * | 2/2010 |

OTHER PUBLICATIONS

Ivy et al ("The Small Intestine in Hunger", from the Hall Physiological Laboratory of the University of Chicago, received for publication Dec. 26, 1924, pp. 99-108). (Year: 1924).*
Non-Final Office Action in corresponding U.S. Appl. No. 14/161,489, dated Aug. 1, 2017.
Do you know to\"Chase\"Benadryl With a Carbonated Drink?, posted on Jun. 1, 2004, http://www.peanutallergy.com/boards/do-you-know-chase-benadryl-with-a-carbonated-drink.

* cited by examiner

*Primary Examiner* — Aaron J Kosar
*Assistant Examiner* — Randall O Winston
(74) *Attorney, Agent, or Firm* — LEASON ELLIS LLP

(57) ABSTRACT

The present invention is directed to a therapeutic composition including an active therapeutic ingredient combined with a liquid or solution based carbonated beverage. The invention as described details the use or administration of the therapeutic composition so as to treat a variety of ailments. The present invention is also directed to a method of administering the therapeutic composition to an individual for the purposes of alleviating an ailment. In a further arrangement, the therapeutic composition is provided to a user as a pre-packaged volume containing a single effective dose of the therapeutic agent.

4 Claims, No Drawings

THERAPEUTIC COMPOSITION INCLUDING CARBONATED SOLUTION

CROSS-REFERENCE TO RELATED PATENT APPLICATION

This application is a Divisional Application of U.S. application Ser. No. 14/161,489, filed Jan. 22, 20214, which is incorporated by reference in its entirety.

The present invention describes a therapeutic composition that includes a therapeutically active ingredient combined with a carbonated solution or beverage. The invention also includes a method of administering and/or formulating a therapeutic composition that includes a therapeutically active ingredient combined with carbonated solution or beverage.

BACKGROUND OF THE INVENTION

It is known in the art to treat various conditions and illnesses using oral medications such as expectorants, non-steroid anti-inflammatory (NSAIDs), antihistamines, cough suppressants, mucolytic agents, curatives, neutraceuticals, and antidotes. These oral therapeutic compositions are supplied to patients in a variety for forms. For example, various medications can be supplied in syrups, liquids, powders, tablets, gels, and other ingestible formats.

However, some medications can have an astringent or bitter taste which discourages patients from taking a full dose. However, the format of the medication (liquid, solid, gel etc.) can be used to make a unpleasant taste One way to increase active ingredient uptake is through the use of carbonation. A carbonated drink is a beverage that has had carbon dioxide introduced for some reason.

The process of carbonating a liquid usually involves the introduction of carbon dioxide under high pressure. When the pressure is reduced, the carbon dioxide is released from the solution as small bubbles, which causes the solution to become effervescent, or "fizz". An example of carbonation is introducing of carbon dioxide in water, resulting in carbonated water.

Currently, carbonation and carbonated beverages are useful in increasing the uptake of certain ingredients in the human body. For example, Schroder et al., *Absorption of calcium from the carbonated dairy soft drink is greater than that from fat-free milk and calcium fortified orange juice in women*, 25 Nutrition Research 737-742 (2005), hereby incorporated by reference in its entirety, describes the use carbonated beverages to increase the absorption of calcium.

Carbonated beverages also can be used to increase the uptake of alcohol. For example, Roberts C. Robinson, *Alcohol concentration and carbonation of drinks: the effect on blood alcohol levels*, 14(7) Journal of Forensic and Legal Medicine 398-405 (2007), hereby incorporated by reference in its entirety, describes increased uptake of alcohol when mixed with carbonated beverages.

The prior art attempts to provide carbonation through the use of effervescent formulations that produce carbonation-like results upon contact with water. However, there are numerous problems associated with effervescent formulations.

For example GB2192790, herein incorporated by reference, describes effervescent formulations comprising from 6 to 32% by weight of acetylcysteine (NAC), from 35 to 50% by weight of citric acid, from 26 to 37% by weight of sodium bicarbonate, from 1 to 1.5% by weight of aspartame and from 5 to 7% by weight of a flavoring agent in which the weight ratio between citric acid and sodium bicarbonate is from 1.2:1 to 1.4:1. The effervescent tablet containing 600 mg of NAC has a total weight of 1900 mg. Similar effervescent tablets are marketed as Fluimucil® 600 and have a total weight of 1.8 g.

EP 0 339 508, herein incorporated by reference, describes mouth-soluble formulations containing NAC, alkaline bicarbonates, carbohydrates and fruit flavorings. The amount of carbohydrates is from 20:1 to 50:1 by weight compared with NAC.

Likewise, EP 0 839 528, herein incorporated by reference, describes mouth-soluble compositions of NAC in which the taste masking is obtained using cyclodextrins. The composition described also contains an amount from 2 to 15 parts of carbohydrates, preferably from 5 to 10 parts by weight compared with NAC. Even low dosage formulations (100-200 g of NAC) have a total weight of at least 2 g.

However, each of these references describes the use of solid form tablets. In each of the cited references, the liquid and solid components are provided for separately, not as a single carbonated beverage.

Therefore, what is needed is a therapeutic composition that includes a carbonated beverage and a therapeutically active ingredient that is, increase uptake of active ingredients, superior product stability, and improve patient compliance, thereby providing a more effective dose and improving compliance with a prescribed dosing regimen. What is further needed is a therapeutic composition that has improved taste presentation over existing therapeutically active compositions.

SUMMARY OF THE INVENTION

The present invention is directed to a therapeutic composition including an active therapeutic ingredient combined with a liquid or solution based carbonated beverage. The invention as described details the use or administration of the therapeutic composition so as to treat a variety of ailments. In one arrangement, the composition described includes a non-steroidal anti-inflammatory drug, such as naproxen combined with a carbonated beverage. The present invention is also directed to a method of administering the therapeutic composition to an individual for the purposes of alleviating an ailment. In a further arrangement, the therapeutic composition is provided to a user as a pre-packaged volume containing a single effective dose of the therapeutic agent.

DESCRIPTION OF ILLUSTRATIVE EMBODIMENTS OF THE INVENTION

By way of overview and introduction, the present invention concerns a therapeutic composition and method for treating various conditions and illnesses using expectorants, anti-inflammatory compounds, antihistamines, herbal supplements, neutraceutical, cough suppressants, mucolytic agents, curatives, and/or antidotes in a composition with a carbonated beverage. More specifically, the present invention is directed to a composition including a therapeutically active ingredient combined with a liquid or solution based carbonated beverage. The invention as described is directed to the use or administration of the described therapeutic composition in order to treat a plurality of ailments through the use of therapeutically active ingredients in combination with a carbonated solution or beverage.

The present invention is also directed to an orally administered therapeutic beverage having excellent physical stability while containing concentrated levels of therapeutically active ingredients. In one arrangement, carbonated beverage operates as a vehicle for solubilizing the therapeutic (for example a pharmaceutically active) ingredient along with a hydrophilic solvent, polyoxyalkylene block copolymers and/or water. These ingredients are, in one arrangement, provided in specific quantities and ratios relative to one another and the therapeutic ingredient such that the therapeutic ingredient is also solubilized and remains so over extended periods of time. Liquid formulations for oral delivery of therapeutic agents are desirable because certain patients, such as children and the elderly, are unable to swallow capsules or tablets.

In a particular formulation, the hydrophilic solvents and water are configured in sufficient quantities and ratios so as to facilitate the incorporation of other compounds, such as sweetening agents and/or other stabilizers, into the composition of the present invention.

The present invention also describes a single use; premeasured volume of the carbonated therapeutic composition configured designed to provide a full and accurate dose of the active ingredient(s).

It is also known in the art that by introducing carbonation to a therapeutic ingredient in a beverage form, the stability will be increased which can lead to a better shelf life for patients, pharmacies, hospitals, and other medical organizations. In one configuration, the carbonation of the beverage increases the acidity and lowers the pH of the therapeutic composition promoting a long shelf-life.

Those skilled in the art will appreciate that by introducing carbonation to a therapeutic ingredient in a beverage form, increased absorption and faster onset of the therapeutic occurs, which provides a significant benefit any patient.

Furthermore, rapid absorption of the active therapeutic ingredient also occurs in the stomach and intestines when combined with a carbonated formulation. In the present invention this absorption is enhanced by the presence of dissolved $CO_2$ in which forms the carbonation component of the beverage.

Although carbonation is a naturally occurring phenomenon in some fermented beverages and natural mineral waters, for the purposes of this invention, carbonation is the considered the deliberate introduction of $CO_2$ gas under pressure to the beverage, such as water, with which the beverage is prepared. The process of infusing gaseous carbon dioxide ($CO_2$) into liquids to produce a carbonated beverage, i.e. carbonation, is well known in the prior art.

The solubility of $CO_2$ in water is a function of temperature and pressure. At a standard pressure of 1 atmosphere (Atm.) and a temperature of 15.60 C, water will dissolve a quantity of $CO_2$ equal to its own volume (i.e. 1.86 g of dissolved $CO_2$). This serves as the basis to describe levels of carbonation in carbonated beverages, based on gas volumes.

Typically in carbonated soft drinks, different gas volumes are characteristic of different flavors. The more acidic flavors such as colas, lemonades, tonic and soda waters typically have gas volumes between 3.0 and 4.0. The sweeter fruit flavors and those of cream sodas have lower carbonation levels typically in the range of 2.5 to 2.8 gas volume and sparkling mineral waters often less and 2.0 gas volumes as described in (Shachman, M.)(2005) The Soft Drinks Companion—A Technical Handbook for the Beverage Industry, CRC Press, Boca Raton, Fla., U.S.A.; pp. 167-177, herein incorporated by reference in its entirety.

When dissolved in water, $CO_2$ forms carbonic acid which, although a weak acid, does have a pH lowering effect. There are several advantages of the formation of the carbonic acid, it contributes to the characteristic acid note of carbonated beverages, it has a contributory effect in troubling the growth of undesirable micro-organisms, and most importantly, it releases $CO_2$ to provide the effervescent effect during consumption.

In one potential arrangement, the carbonated beverage of the present invention contains additives such as natural flavors, artificial flavors or sweeteners, stabilizers, or consumable acids. Furthermore, in some arrangements, the carbonated beverage will contain caffeine. For example, the caffeine content of the carbonated beverage is about 43/mg.

Those skilled in the art will recognize that a variety of therapeutic ingredients are suitable for inclusion into the carbonated therapeutic beverage described. For instance, it is possible to include effective single dosage, or extra strength dosages of therapeutically active ingredients such as dextromethorphan, pseudoephedrine, acetaminophen, terfenadine, guaifenesin, trimethoprim, prednisolone, ibuprofen, prednisolone sodium phosphate, methacholine, neostigmine, epinephrine, albuterol, pseudoephedrine hydrochloride, diphenhydramine, chlorpheniramine maleate, phenothiazine, chlorpromazine, chlordiazepoxide, amitriptyline, barbiturates, diphenylhydantoin, morphine, demerol, codeine, lomotil, lidocaine, salicylic acid, sulfonamides, prednisolone sodium phosphate, chloroquine, vitamin preparations, minerals, antibiotics compounds, antiadrenergic compounds, antiserotonergic compounds, anticholinergic compounds, antihistaminergic compounds, antipsychotic compounds, anti-depressive compounds and herbal supplements.

Acetylcysteine

As an example of the present invention, the carbonated therapeutic composition contains acetylcysteine (or N-acetylcysteine). More specifically, the therapeutic composition relates to a carbonated beverage composition containing acetylcysteine in a single dose. Those skilled in the art will appreciate that the quantity of the active therapeutic ingredient is selected based on different dosage strength formulations. For example, one dosage formulation has a regular strength quantity. Alternatively, a different formulation has an extra strength formulation. For example, in one arrangement, a carbonated therapeutic composition is provided wherein the amount of acetylcisteine is at least 300 mg.

Furthermore, those skilled in the art are aware that some therapeutic ingredients or agents, such as N-acetylcisteine (NAC), have its unpleasant taste which is difficult to mask. This is especially true in high dosage formulations (such as 600 mg formulations of N-acetylcisteine).

The present invention describes a carbonated beverage having a high dosage (for example, a 600 mg dosage of N-acetylcisteine) of the therapeutic component. In this high-strength dosage formulation, the carbonated therapeutic beverage or solution also includes additional or complementary compounds to adjust the flavor profile or organoleptic properties of the beverage in order to provide increased compliance with the dosage regimen.

In a further arrangement, a carbonated therapeutic composition is prepared with a dosage range for a given therapeutic agent (for example, naproxen in the amount of 50-800 mg per day) depending upon the necessary requirements of the user. In this arrangement, a suitable combination of elements will be combined so as to provide a palatable or desired flavor to the composition.

In an alternative arrangement, the carbonated therapeutic composition includes the use of sweeteners and/or flavoring profile modification agents in quantities sufficient to provide a particular flavor or flavor profile (for example, orange or grape-flavored) designed to enhance administration compliance of the therapeutic agent.

The unpleasant tastes of some therapeutic compounds result from degradation products (mainly sulphides and disulphides). This unpleasant taste is more pronounced when the therapeutic form is stored for extended periods at high temperatures. One feature of the present invention is to address unpleasant flavor outcomes in therapeutic compounds (such as N-acetylcisteine) by combining the carbonated therapeutic composition with a flavoring and stabilizing agents in sufficient ratios and quantities so as to mask the taste of a single dosage volume of the therapeutic compound, but sufficiently stabilizing so as to provide increased shelf-life of the carbonated therapeutic composition in variable temperature settings.

Those skilled in the art will appreciate that alternative forms and dosage ranges of the described carbonated therapeutic composition is contemplated and envisioned. By way on non-limiting example, the following formulations and compounds are exemplary of the present invention.

Diphenhydramine

In one arrangement, the carbonated therapeutic composition contains diphenhydramine More particularly, the present invention relates to a carbonated therapeutic composition beverage containing diphenhydramine in a single dose regular or extra strength formulation. Diphenhydramine is known chemically as 2-(benzhydroxyl)-N,N-dimethylethylamine. However, those skilled in the art will appreciate that alternative forms and arrangements of the described compound are envisioned and understood. It is also known in the art to make that the uses of sleep aid, antiemetic, or as an antihistamine Those skilled in the art will appreciate that alternative forms, dosage ranges and compositions necessary to provide an effect amount of the therapeutic composition in order to achieve these therapeutic results in a variety of different age groups, body types and health states.

Brompheniramine

In a further arrangement, a carbonated beverage formulation including a therapeutic agent is provided wherein the therapeutic agent is brompheniramine, (and optionally pseudoephedrine and dextromethorphan). In one arrangement the therapeutic agent is provided in a quantity sufficient for a single use, regular strength dose. In a further arrangement, the composition described contains at least 10 ml of brompheniramine.

Those skilled in the art will appreciate that alternative forms, dosage ranges and arrangements of the described carbonated formulation including the described therapeutic ingredient are envisioned and understood.

Dextromethorphan

In a further arrangement of the invention described, the therapeutically active ingredient of the carbonated therapeutic compound is dextromethorphan. In one envisioned therapeutic beverage formulation, the carbonated beverage contains a range of effective amounts of dextromethorphan. Those skilled in the art will appreciate that some uses of dextromethorphan is used as an antitussive.

However, those skilled in the art will appreciate that alternative forms, dosages quantities and arrangements of the described compound are envisioned and understood.

Guaifenesin

In a further arrangement of the invention described, the carbonated therapeutic compound includes guaifenesin. Those skilled in the art will appreciate that in one arrangement, the active ingredient of a given therapeutic compound is guaifenesin. In one envisioned therapeutic beverage formulation, the carbonated beverage contains a range of effective amounts of guaifenesin. For example, the active ingredient is included in sufficient quantities for a regular, extra-strength, or child dosages. Those skilled in the art will appreciate that some uses of guaifenesin are as a mucolytic and expectorant.

However, those skilled in the art will appreciate that alternative forms, dosages quantities and arrangements of the described compound are envisioned and understood.

Ibuprophen

In a further arrangement of the invention described, the carbonated therapeutic compound includes ibuprophen. Those skilled in the art will appreciate that in one arrangement, the active ingredient of a given therapeutic compound is ibuprophen. In one envisioned therapeutic beverage formulation, the carbonated beverage contains a range of effective amounts of ibuprophen. For example, the active ingredient is included in sufficient quantities for a regular, extra-strength, or child dosages. Those skilled in the art will appreciate that some uses of ibuprophen are as an antitussive.

However, those skilled in the art will appreciate that alternative forms, dosages quantities and arrangements of the described compound are envisioned and understood.

Meclizine

In a further arrangement of the invention described, the carbonated therapeutic compound includes meclizine. Those skilled in the art will appreciate that in one arrangement, the active ingredient of a given therapeutic compound is meclizine. In one envisioned therapeutic beverage formulation, the carbonated beverage contains a range of effective amounts of meclizine. For example, the active ingredient is included in sufficient quantities for a regular, extra-strength, or child dosages. Those skilled in the art will appreciate that some uses of Meclizine are as an antiemetic.

However, those skilled in the art will appreciate that alternative forms, dosages quantities and arrangements of the described compound are envisioned and understood.

Caffeine

In a further arrangement of the invention described, the carbonated therapeutic compound includes caffeine. Those skilled in the art will appreciate that in one arrangement, the active ingredient of a given therapeutic compound is caffeine. In one envisioned therapeutic beverage formulation, the carbonated beverage contains a range of effective amounts of caffeine. For example, the active ingredient is included in sufficient quantities for a regular, extra-strength, or child dosages. Those skilled in the art will appreciate that some uses of caffeine are as a stimulant.

However, those skilled in the art will appreciate that alternative forms, dosages quantities and arrangements of the described compound are envisioned and understood.

Acetaminophen

In a further arrangement of the invention described, the carbonated therapeutic compound includes acetaminophen. Those skilled in the art will appreciate that in one arrangement, the active ingredient of a given therapeutic compound is acetaminophen. In one envisioned therapeutic beverage formulation, the carbonated beverage contains a range of effective amounts of acetaminophen. For example, the active ingredient is included in sufficient quantities for a regular, extra-strength, or child dosages. Those skilled in the art will appreciate that some uses of acetaminophen are as an analgesic.

However, those skilled in the art will appreciate that alternative forms, dosages quantities and arrangements of the described compound are envisioned and understood.

Dimenhydrinate

In a further arrangement of the invention described, the carbonated therapeutic compound includes dimenhydrinate. Those skilled in the art will appreciate that in one arrangement, the active ingredient of a given therapeutic compound is dimenhydrinate. In one envisioned therapeutic beverage formulation, the carbonated beverage contains a range of effective amounts of dimenhydrinate. For example, the active ingredient is included in sufficient quantities for a regular, extra-strength, or child dosages. Those skilled in the art will appreciate that some uses of dimenhydrinate are as an antihistamine, antiemetic, and sleep aid.

However, those skilled in the art will appreciate that alternative forms, dosages quantities and arrangements of the described compound are envisioned and understood.

Doxylamine

In an alternative arrangement of the invention described, the therapeutically active ingredient of the carbonated therapeutic compound is doxylamine Those skilled in the art will appreciate that doxylamine, can be described by the chemical name (flS)-A/,A/-dimethyl-2-(1-phenyl-1-(pyridin-2-yl) ethoxy) ethanamine. In one arrangement, the carbonated therapeutic composition contains doxylamine in sufficient quantities in order to be effective for the management of insomnia. Those skilled in the art will appreciate that doxylamine is applicable as a sleep aid, antiemetic and/or antihistamine.

However, those skilled in the art will appreciate that alternative forms, dosages quantities and arrangements of the described compound are envisioned and understood.

Naproxen

In an alternative arrangement of the invention described, the therapeutically active ingredient of the carbonated therapeutic compound is naproxen. Those skilled in the art will appreciate that in one composition or formulation the described carbonated beverage contains an effective therapeutic quantity of naproxen. Naproxen is known as a Non-steroidal anti-inflammatory.

However, those skilled in the art will appreciate that alternative forms, dosages quantities and arrangements of the described compound are envisioned and understood.

Pseudoephedrine

In an alternative arrangement of the invention described, the therapeutically active ingredient of the carbonated therapeutic compound is pseudoephedrine. In a further arrangement the pseudoephedrine component of the therapeutic compound is pseudoephedrine. In one configuration the carbonated beverage therapeutic composition comprising pseudoephedrine also includes a liquid excipient base. It is well known in the art that pseudoephedrine is used as a decongestant.

However, those skilled in the art will appreciate that alternative forms, dosages quantities and arrangements of the described compound are envisioned and understood.

Yohimbe Bark Extract

A further embodiment of the carbonated therapeutic composition includes Yohimbe barkextract. It is also known in the art that Yohimbe bark increases blood flow.

However, those skilled in the art will appreciate that alternative forms, dosages quantities and arrangements of the described compound are envisioned and understood.

In further or alternative arrangements, the compositions so described also include vitamins. For example, the carbonated composition includes a therapeutically or therapeutically active ingredient in combination with a vitamin, such as an A or B-series vitamin B6 (pyridoxine) or B3 (Niacin).

In further or alternative arrangements, the compositions so described also include elements such as aluminum, calcium as well as antifoaming agents such as simethicone. Those skilled in the art will appreciate that that consumable quantities of aluminum, has antacid functions. Furthermore, those skilled in the art will appreciate that calcium, in consumable quantities, has antacid functions. Those skilled in the art will also appreciate that simethicone and other anti-foaming agents have anti-flatulent functions.

In one arrangement the carbonated therapeutic composition has at least two active ingredients configured to work in a synergistic manner so as to alleviate multiple symptoms afflicting a user. In a further configuration, the pH value of the carbonated beverage is below 7. In a further configuration, the pH value of the carbonated beverage is below 4. In a further configuration of the beverages described, the gas volume is at least 2. In an additional example of the foregoing, the gas volume is at least 3.

In further or alternative arrangements, the compositions so described also include herbal supplements. For example, and in no way limiting, the described compositions, in one particular composition, include one or more of Aloe Vera, Bilberry, Black Cohosh, Cat's Claw, Chaste berry, Cranberry, Dandelion, Echinacea, Ephedra, Evening Primrose Oil, Feverfew, Flaxseed/Flaxseed, Oil, Garlic, Ginger, Ginkgo, Ginseng Asian, Goldenseal, Green Tea, Hawthorn, Horse Chestnut, Kava, Licorice, Root Milk Thistle, Mistletoe, Red Clover, Saw Palmetto, St. John's Wort and/or Valerian. These optional ingredients are included in the composition in an amount sufficient to perform their intended function without compromising the benefits associated with the present invention.

The carbonated therapeutic composition, in one or more arrangements, includes optional ingredients traditionally included in orally administered beverage compositions. These optional ingredients include, but are not limited to, dyes, fragrances, preservatives, antioxidants, and similar types of compounds. Specific optional ingredients include, but, are not restricted to surfactants including tyloxapol, polysorbate 80, lauroglycol 90, polyox 40 stearate, capryol 90, polymers including polyvinylpyrrolidone, hydroxypropyl methyl cellulose, beta-cyclodextrins, or solvents, such as propylene carbonate, n-methylpyrrolidone, transcutol, dimethylisosorbide and mixtures thereof. These optional ingredients are included in the composition in an amount sufficient to perform their intended function without compromising the benefits associated with the present invention.

While the invention has been particularly shown and described with reference to a preferred embodiment thereof, it will be understood by those skilled in the art that various changes in form and details may be made therein without departing from the spirit and scope of the invention.

What is claimed:

1. A method of administering a medicament, the method comprising:
    administering to a subject having a medical condition in need of therapeutic treatment, a therapeutically effective aqueous beverage composition consisting of: a carbonated liquid having a gas volume of at least 2.0; dextromethorphan or therapeutically acceptable salt thereof; at least one preservative and at least one flavoring agent, where the dextromethorphan is available for immediate release and absorption in the stomach upon ingestion , wherein the at least one flavoring agent and at least one preservative does not prevent immediate release and absorption of dextromethorphan, wherein the aqueous composition has a pH less than 4.

2. The method of claim 1, wherein the medical condition is nausea.

3. A method of administering a medicament, the method comprising:

administering to a subject having a medical condition in need of therapeutic treatment, a therapeutically effective aqueous beverage composition consisting of: a carbonated liquid having a gas volume of at least 2.0; dextromethorphan or therapeutically acceptable salt thereof doxylamine or a therapeutically acceptable salt thereof, one or more preservatives and at least one flavoring agent, where the dextromethorphan and doxylamine are available for immediate release and absorption in the stomach upon ingestion; and wherein the at least one flavoring agent and at least one preservative does not prevent immediate release and absorption of doxylamine and the aqueous composition has a pH less than 4.

4. The method of claim 3, wherein the medical condition is nausea.

\* \* \* \* \*